United States Patent
Fukuzumi et al.

(10) Patent No.: US 7,550,246 B2
(45) Date of Patent: Jun. 23, 2009

(54) PHOTOACID GENERATOR

(75) Inventors: Shunichi Fukuzumi, Toyonaka (JP);
Seiji Ogo, Mino (JP); Tomoyoshi Suenobu, Mino (JP)

(73) Assignee: Japan Science and Technology Agency, Kawaguchi-Shi (JP)

( * ) Notice: Subject to any disclaimer, the term of this patent is extended or adjusted under 35 U.S.C. 154(b) by 0 days.

(21) Appl. No.: 10/573,780

(22) PCT Filed: Sep. 24, 2004

(86) PCT No.: PCT/JP2004/014433

§ 371 (c)(1),
(2), (4) Date: Mar. 28, 2006

(87) PCT Pub. No.: WO2005/030784

PCT Pub. Date: Apr. 7, 2005

(65) Prior Publication Data

US 2007/0059633 A1    Mar. 15, 2007

(30) Foreign Application Priority Data

Sep. 29, 2003  (JP) .................... 2003-338664

(51) Int. Cl.
*G03F 7/00* (2006.01)
*G03F 7/004* (2006.01)
(52) U.S. Cl. .................... 430/270.1; 260/439
(58) Field of Classification Search ............. 260/439; 430/270.1
See application file for complete search history.

(56) References Cited

U.S. PATENT DOCUMENTS

2002/0083643 A1*  7/2002  Amendola et al. ......... 48/61

FOREIGN PATENT DOCUMENTS

JP    2002020426 A  *  1/2002
JP    2004224715 A  *  8/2004

OTHER PUBLICATIONS

Ziessel, Raymond. Photocatalysis. Mechanistic Studies of Homogeneous Photochemical Water Gas Shift Reaction Catalyzed under Mild Conditions by Novel Cationic Iridium (III) Complexes. Journal of American Chemical Society, 1993, vol. 115, pp. 118-122. Received Jul. 21, 1992.*

(Continued)

*Primary Examiner*—Amanda C. Walke
(74) *Attorney, Agent, or Firm*—Birch, Stewart, Kolasch & Birch, LLP

(57) ABSTRACT

A photoacid generator comprising a metal hydride complex represented by the formula (I):

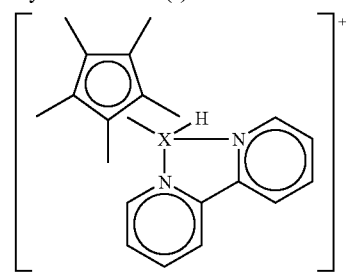

wherein X represents a metal atom. The iridium hydride complex of the present invention can be used as an acid generator for chemically-amplified photoresists or color filters for liquid crystal, and in addition, can be widely applied in photographic-related or printing-related fields, or the like.

22 Claims, 7 Drawing Sheets

OTHER PUBLICATIONS

Lenges, Christian., White, Peter S., Marshall, Will J, and Brookhart, Maurice. Synthesis, Structure, and Reactivity of [C5ME5CoLL'] Complexes with L= Pyridine and L'= Olefin or L-L'=Bipyridine. Organometallics, vol. 19, pp. 1248-1254. Received Oct. 26, 1999, Published on the Web Mar. 10, 2000.*

Caix, Chrystelle et al., Journal of Electroanalytical Chemistry, 1996, vol. 403, No. 1-2, pp. 189 to 202.

G. Pohlers et al., "Chem. Mater.". 1997, vol. 9, No. 6, pp. 1353-1361.

Tsutomu Abura et al., J. Am. Chem. Soc., 2003, 125(14), pp. 4149-4154.

Zalis et al., Inorganic Chemistry, vol. 42, No. 17, 2003, pp. 5185-5191. XP-002502528.

* cited by examiner

PHOTOACID GENERATOR

TECHNICAL FIELD

The present invention relates to a photoacid generator. More specifically, the present invention relates to a photoacid generator which efficiently generates an acid upon irradiation of light. The photoacid generator can be suitably used in chemically-amplified photoresists, color filters for liquid crystal or the like.

BACKGROUND ART

As the photoacid generator for use in chemically-amplified photoresists, color filters for liquid crystal and the like, paramethoxystyryl triazine has been conventionally known (see, for example, G. Pohlers et al, "Chem. Mater.", 1997, 9(6), pp. 1353-1361).

Although paramethoxystyryl triazine is highly sensitive, it is disadvantageous in terms of unfavorable solubility and compatibility with a solvent.

DISCLOSURE OF THE INVENTION

The present invention has been accomplished in view of the above-mentioned prior art, and an object of the present invention is to provide a photoacid generator showing excellent solubility in an organic solvent or water, as well as being highly sensitive to visible light.

The present invention relates to a photoacid generator comprising a metal hydride complex represented by the formula (I):

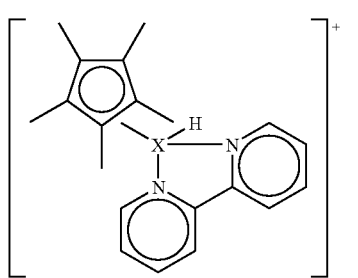

wherein X represents a metal atom.

BEST MODE FOR CARRYING OUT THE INVENTION

The photoacid generator of the present invention comprises a metal hydride complex represented by the formula (I) (hereinafter simply referred to as "metal hydride complex"). In the formula (I), X represents a metal atom. Examples of preferred metal atoms include iridium, ruthenium, rhodium and cobalt. Among them, iridium is preferable.

The metal hydride complex exhibits excellent solubility in an organic solvent or water, as well as being highly sensitive to visible light. Therefore, the photoacid generator of the present invention may be those including a metal hydride complex alone, or those including a metal hydride complex dissolved in an organic solvent or water.

Examples of the organic solvent include polar organic solvents such as acetonitrile; primary alcohols typified by methanol and ethanol; secondary alcohol typified by isopropyl alcohol; tertiary alcohols typified by t-butyl alcohol; polyhydric alcohols typified by ethylene glycol; dimethyl formamide; dimethyl sulfoxide; and ethyl acetate. However, the present invention is not limited only to the illustrative examples.

When the photoacid generator of the present invention is in the form of a solution of a metal hydride complex, the concentration of the metal hydride in the solution is not particularly limited. However, it is desired to be usually 0.1 to 5% by weight, and preferably 0.5 to 3% by weight.

The metal hydride complex is a compound which can be readily obtained by easily synthesizing in accordance with a method described, for example, on page 4150 in Watanabe et al, "J. Am. Chem. Soc.", 2003, 125(14), pp. 4149-4154.

EXAMPLES

The metal hydride complex of the present invention will be hereinafter specifically explained on the basis of Examples, without intending to limit the scope of the present invention only to these Examples.

Preparation Example 1

An iridium hydride complex was prepared according to a method described on page 4150 in Watanabe et al, "J. Am. Chem. Soc.", 2003, 125(14), pp. 4149-4154.

The resulting compound was confirmed to be an iridium hydride complex with agreement of the $^1$H-NMR data of the resulting compound with the $^1$H-NMR data described in the aforementioned document, on page 4150.

Example 1

The iridium hydride complex obtained in the Preparation Example 1 was dissolved in degassed methanol to prepare a solution having a concentration of the iridium hydride complex of $2.4 \times 10^{-4}$ M.

The resulting solution was irradiated with a laser beam having a wavelength λ of 430 nm at 10 mJ/pulse to excite the iridium hydride complex. After 10 μs, 4 ms or 12 ms passed from the irradiation of the laser beam, transient absorption spectrum at the wavelength of 300 to 800 nm was examined. The results are shown in FIG. 1.

Figure 1:
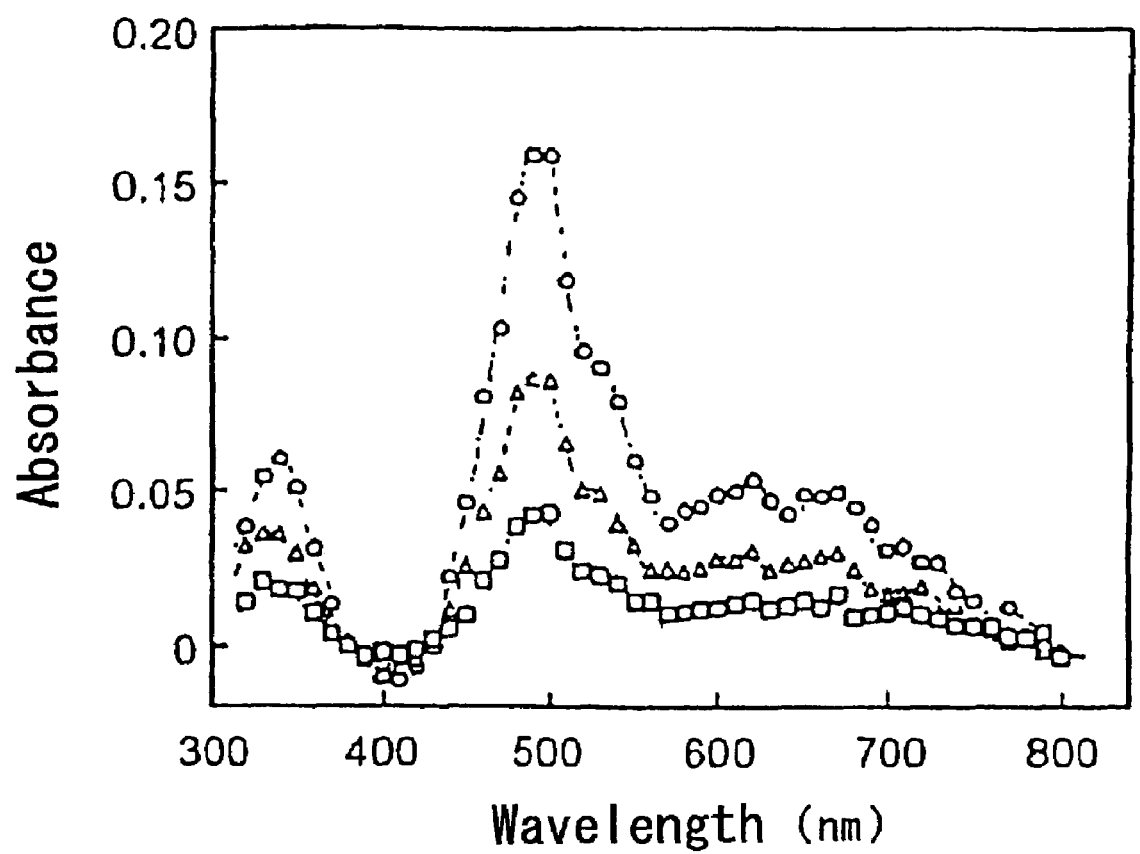
FIG. 1 is a graph showing a relationship between the absorbance and the wavelength in the transient absorption spectrum of an iridium hydride complex.

In FIG. 1, open circle (◯) indicates the data after 10 μs passed from the irradiation of the laser beam; open triangle (Δ) indicates the data after 4 ms passed from the irradiation of the laser beam; and the open square (□) indicates the data after 12 ms passed from the irradiation of the laser beam. These transient absorption spectra were compared with the absorption spectra described in the document [M. Ladwig et al, "*J. Organomet. Chem.*", 1992, 439(1), pp. 79-90], and consequently, were confirmed to be the iridium complex represented by the formula (II):

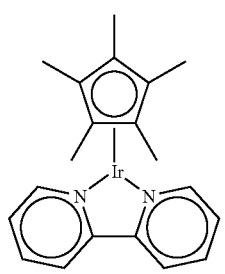

(II)

(hereinafter simply referred to as "iridium complex").

Also, it can be seen from the results shown in FIG. 1 that the iridium hydride complex efficiently serves as a photoacid generator because deprotonation of the iridium hydride complex takes place in its excited state to efficiently generate an acid upon irradiation of the laser beam as shown in the following Scheme 1.

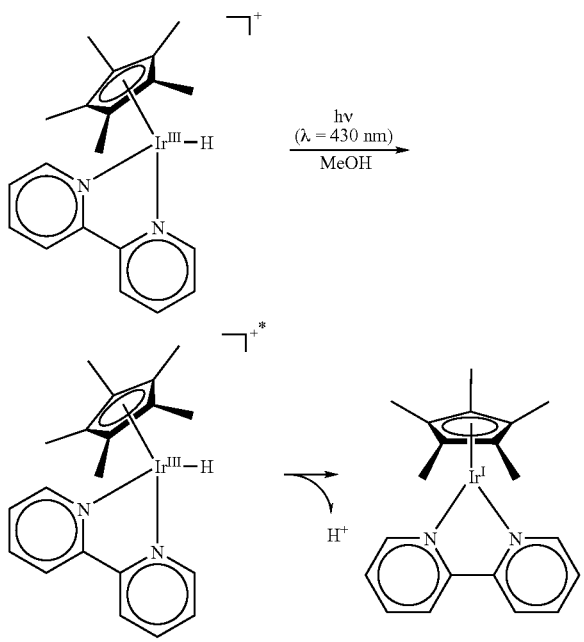

Example 2

The iridium hydride complex obtained in the Preparation Example 1 was dissolved in degassed methanol or $CH_3OD$ to prepare a solution having a concentration of the iridium hydride complex of $2.4 \times 10^{-4}$ M.

The resulting solution was irradiated with a laser beam having a wavelength of 430 nm at 10 mJ/pulse to excite the iridium hydride complex. Change with time of the absorbance at the wavelength of 490 nm was examined. The results are shown in FIG. 2.

Figure 2:
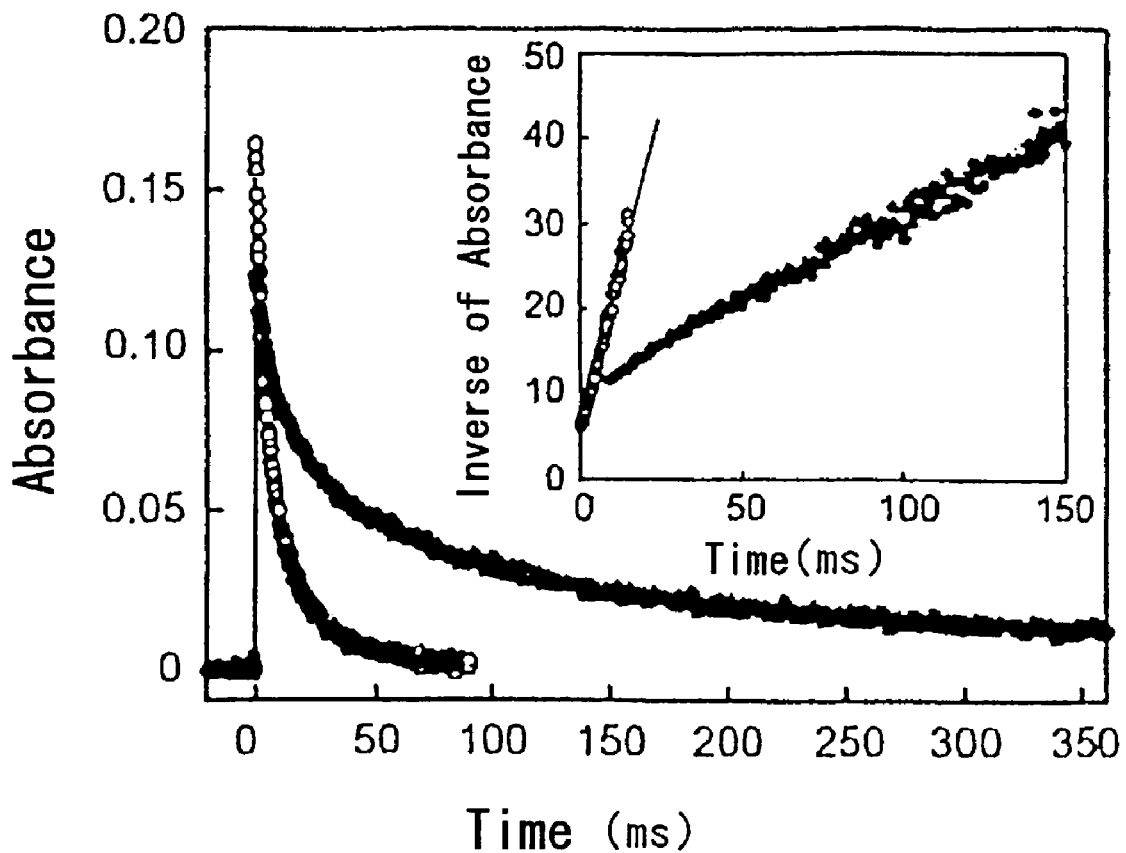
FIG. 2 is a graph showing change with time of the absorbance of an iridium complex.

FIG. 2 shows the attenuation of the iridium complex produced by irradiation of the iridium hydride complex with the laser beam in degassed methanol (in the figure, open circle ◯) and $CH_3OD$ (in the figure, solid circle ●), at the wavelength of 490 nm in the transient absorption spectrum. This attenuation complies with second-order reaction kinetics.

It can be seen from the results shown in FIG. 2 that the rate of attenuation of the iridium complex is notably delayed when $CH_3OD$ is used instead of methanol ($CH_3OH$).

In FIG. 2, the figure incorporated at the upper right portion is a graph showing the second-order plot of the absorbance (time dependency of inverse of absorbance) when the iridium hydride complex was irradiated with the laser beam. From the slope of the second-order plot shown in FIG. 2, a large kinetic deuterium isotope effect ($k_H/k_D = 8.2$) was determined.

Example 3

After producing the iridium complex and proton through deprotonation of the iridium hydride complex in the similar manner as in Example 1, this iridium complex was protonated by trifluoromethanesulfonic acid in methanol. As a result, the iridium hydride complex was produced in the ground state.

Figure 3:
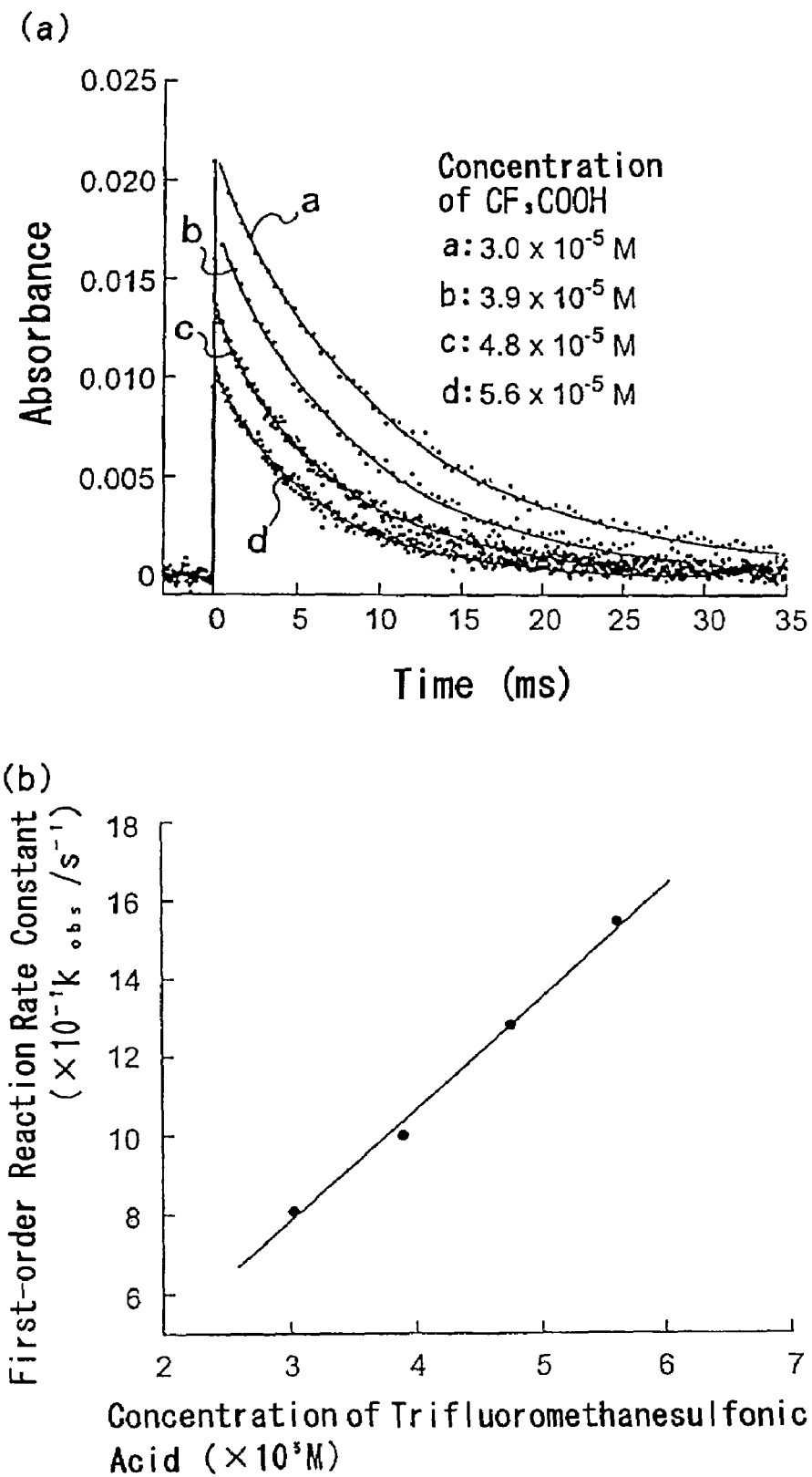
FIG. 3(a) is a graph showing change with time in attenuation of the absorbance in the transient absorption spectrum of an iridium hydride complex.
FIG. 3(b) is a graph showing dependency on the concentration of trifluoromethanesulfonic acid of a first-order reaction rate constant determined from FIG. 3(a).

In the presence of trifluoromethanesulfonic acid at various concentrations ($3.0 \times 10^{-5}$ M, $3.9 \times 10^{-5}$ M, $4.8 \times 10^{-5}$ M or $5.6 \times 10^{-5}$ M), change with time in attenuation of the absorbance in the transient absorption spectrum of the $2.4 \times 10^{-4}$ M iridium hydride complex at a wavelength of 490 nm was determined. The results are shown in FIG. 3(a). Also, dependency on the trifluoromethanesulfonic acid concentration of the first-order reaction rate constant determined from change with time of this attenuation of the absorbance is shown in FIG. 3(b).

As shown in FIG. 3(a), it can be seen that the attenuation of the transient absorption spectrum of the iridium hydride complex complies first-order reaction kinetics in the presence of trifluoromethanesulfonic acid ($3.0 \times 10^{-5}$ M, $3.9 \times 10^{-5}$ M, $4.8 \times 10^{-5}$ M or $5.6 \times 10^{-5}$ M).

Furthermore, it can be seen from the results shown in FIG. 3(b) that the first-order reaction rate constant increases linearly according to the increase in the concentration of trifluoromethanesulfonic acid.

It can be seen from these results that deprotonation of the iridium hydride complex and protonation of the iridium complex take place upon irradiation of the iridium hydride complex with visible light.

Example 4

The iridium hydride complex was dissolved in degassed methanol to prepare a solution having a concentration of the iridium hydride complex of $1.5 \times 10^{-4}$ M.

Figure 4:
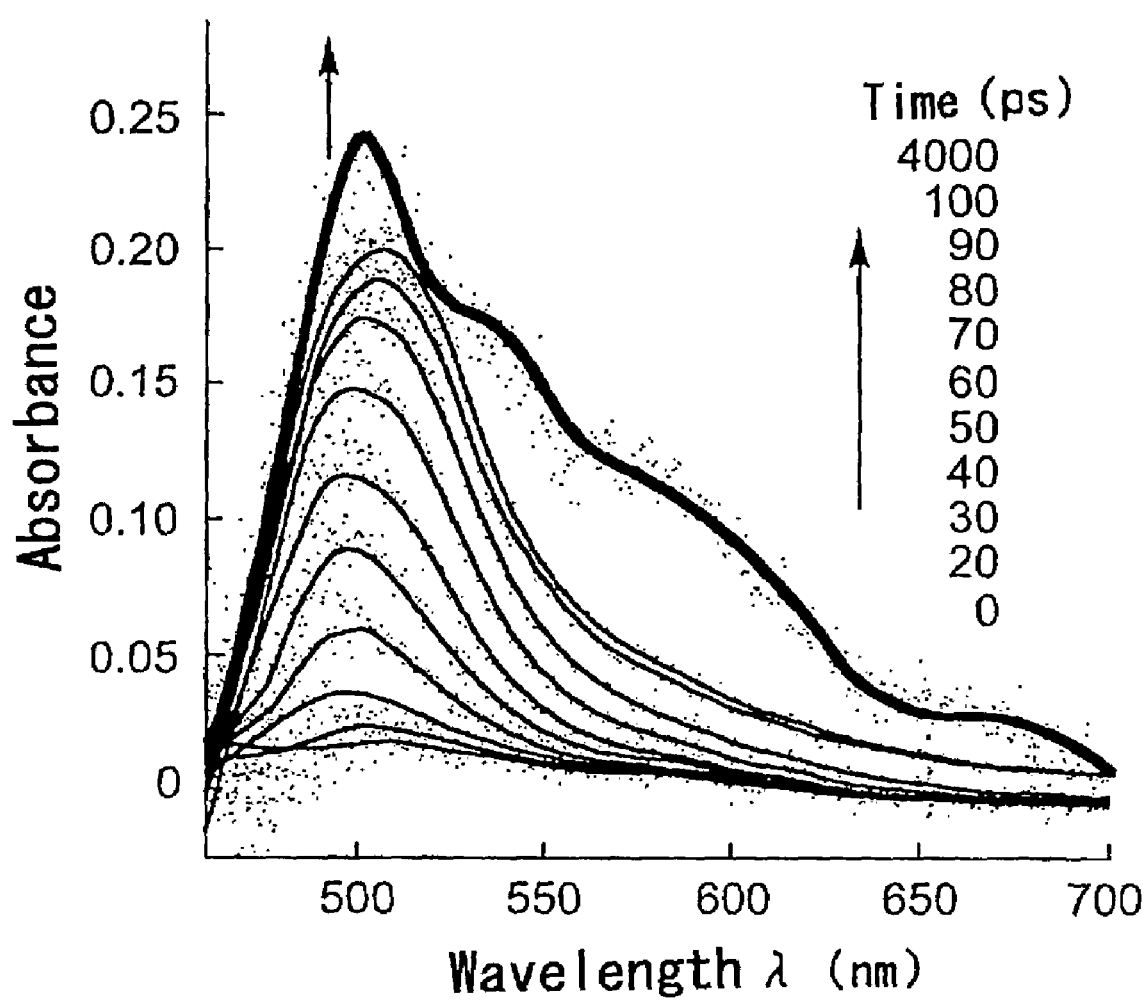
FIG. 4 is a graph showing the picosecond time-resolved transient absorption spectrum of an iridium hydride complex.

Next, the resulting solution was irradiated with a laser beam having a wavelength of 355 nm at 1.5 mJ/pulse to excite the iridium hydride complex. Therefore, production of the excited state and photoacid generation of the iridium hydride complex were observed from alteration of the transient absorption spectrum by picosecond laser flash photolysis. The results are shown in FIG. 4. In FIG. 4, each transient absorption spectrum is represented as the results at each time passed, in the direction indicated by the arrowhead in the figure.

It can be seen from the results of the picosecond time-resolved transient absorption spectrum shown in FIG. 4 that increase in absorption band derived from production of the excited state of the iridium hydride complex having an absorption maximum at a wavelength of 500 nm is found up to 100 ps from the irradiation of the laser beam.

Example 5

Change with time in increase of the absorbance at a wavelength of 500 nm in the picosecond time-resolved transient absorption spectrum of the iridium hydride complex was determined up to the time of 200 ps, in the same manner as in Example 4. The results are shown in FIG. 5.

Figure 5:
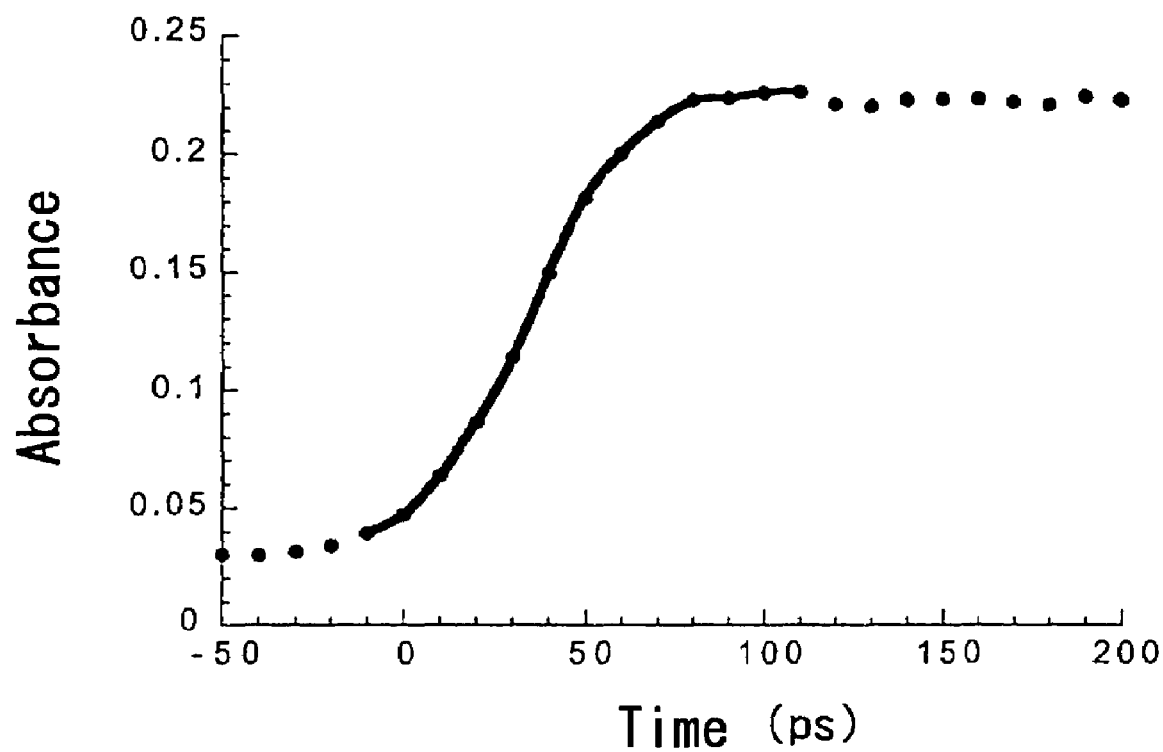
FIG. 5 is a graph showing change with time in increase of the absorbance at a wavelength of 500 nm in the picosecond time-resolved transient absorption spectrum of an iridium hydride complex.

It can be seen from the results shown in FIG. 5 that this change in the absorbance complies the first-order reaction kinetics, and the first-order reaction rate constant is determined to be $1.4 \times 10^{10}$ s$^{-1}$.

Example 6

Figure 6:
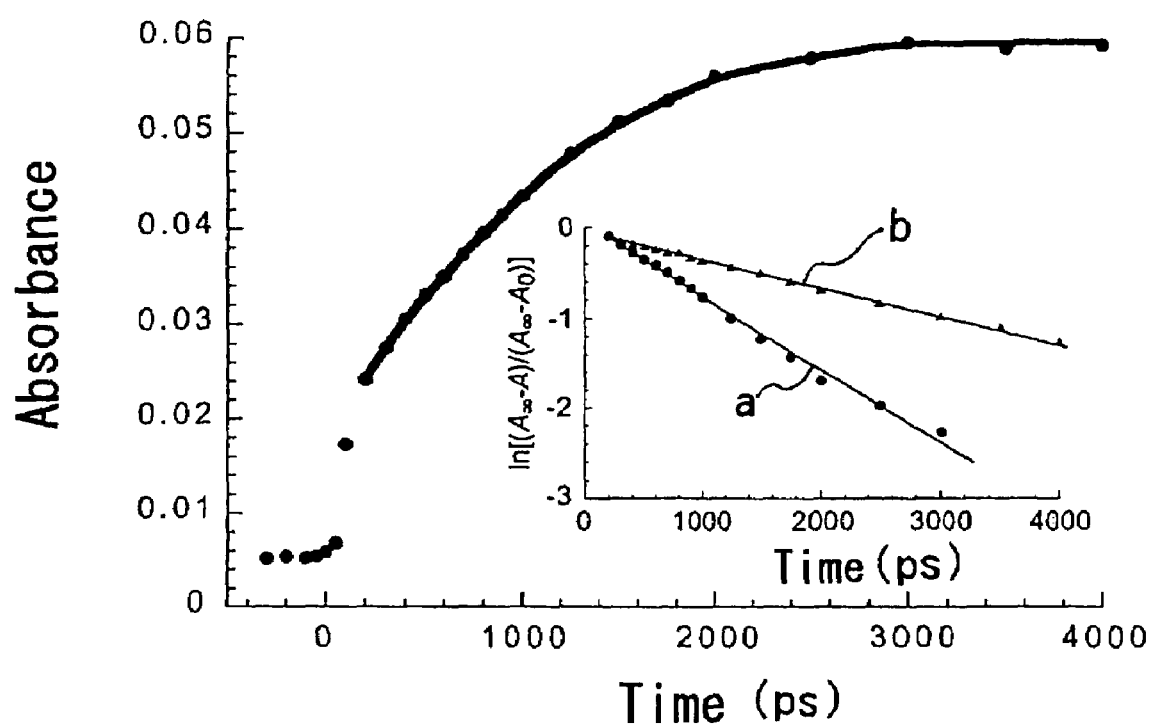
FIG. 6 is a graph showing change with time in increase of the absorbance at a wavelength of 575 nm in the picosecond time-resolved transient absorption spectrum of an iridium hydride complex.

Change with time in increase of the absorbance at a wavelength of 575 nm in the picosecond time-resolved transient absorption spectrum of the iridium hydride complex was determined from irradiation of the light up to the time of 4000 ps, in the same manner as in Example 4. The results are shown in FIG. 6. In FIG. 6, in the inserted figure at the right bottom portion thereof, "a" shows the first-order plot of change with time of the absorbance in the case of the iridium hydride complex, and "b" shows the first-order plot of change with time of the absorbance in the case of the deuterated iridium hydride complex.

tration in the photoinduced exchange reaction between hydrogen and deuterium of the iridium hydride complex was determined. The results are shown in FIG. 7.

Figure 7:
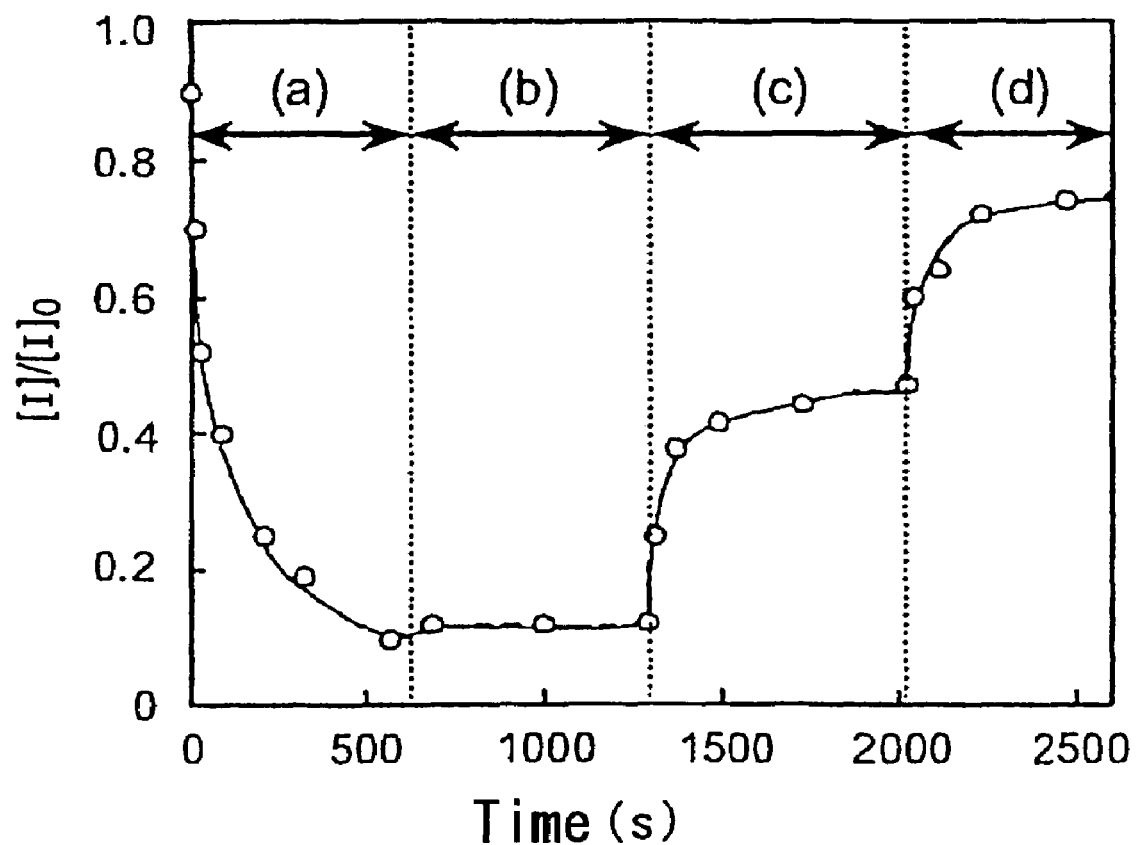
FIG. 7 is a graph showing change with time of ratio ([I]/[I]$_0$) of the concentration of an iridium hydride complex to the initial concentration.

It can be seen from the results shown in FIG. 7 that the $^1$H-NMR signal at −10.7 ppm ascribed to proton of the hydride of the iridium hydride complex disappears with passage of time from the irradiation of the ray, when the solution of the iridium hydride complex in CH$_3$OD is irradiated with the ray in its steady state, as shown in the region "a" in FIG. 7.

Next, to the solution of 0.6 mL irradiated with the ray was added 0.15 mL of water [H$_2$O/CD$_3$OD=1:4 (volume ratio)], and kept in a dark place. As a result, as shown in the region "b" in FIG. 7, no alteration in the $^1$H-NMR signal was caused.

Moreover, when the aforementioned solution was irradiated as a sample with a monochromatic visible ray having a wavelength of 430 nm, proton of the hydride of the iridium hydride complex appeared again as shown in the region "c" in FIG. 7.

Furthermore, when 0.15 mL of water [H$_2$O/CD$_3$OD=1:2 (volume ratio)] was added to 0.75 mL of the aforementioned solution, and the resulting solution was irradiated as a sample with the monochromatic visible ray having a wavelength of 430 nm, the proton signal of the hydride increased to 80% of the amount of the charged iridium hydride complex represented by the formula (I), as shown in the region "d" in FIG. 7.

From the foregoing results, it can be seen that exchange between hydrogen and deuterium of the iridium hydride complex in the steady state in CD$_3$OD efficiently takes place as shown in the following Scheme 2.

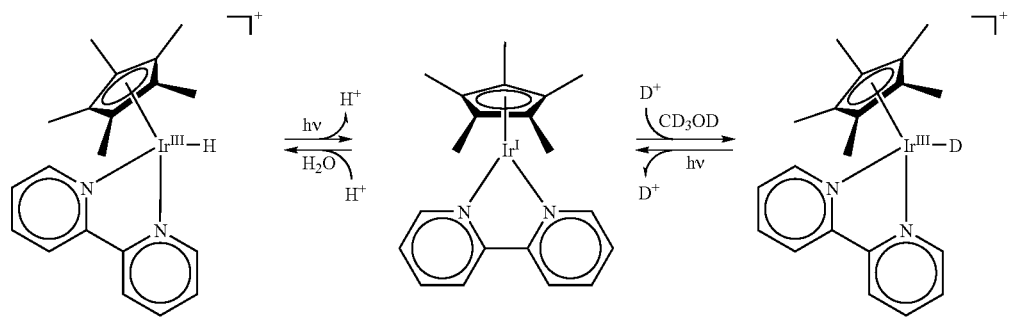

Scheme 2

It can be seen from the results shown in FIG. 6 that the transient absorption spectrum ascribed to the production of the iridium complex by deprotonation from the iridium hydride complex is increased upon generation of the photoacid from the excited state of the iridium hydride complex after 4000 ps passed from the irradiation of the light. Also, this change in the absorbance complies the first-order reaction kinetics, and the rate of generation of the photoacid from the excited state of the iridium hydride complex calculated from the slope of the first-order plot is determined to be $8.1 \times 10^8$ s$^{-1}$.

Example 7

A 0.6 mL solution including the iridium hydride complex ($8.2 \times 10^{-3}$ M) dissolved in degassed CD$_3$OD was irradiated with a monochromatic visible ray having a wavelength of 430 nm, and change with time of the ratio ([I]/[I]$_0$) of the concentration of the iridium hydride complex to the initial concen-

Example 8

When 0.6 mL of a $8.2 \times 10^{-3}$ M iridium hydride complex solution in CD$_3$OD was irradiated with a faint monochromatic light (wavelength: 430 nm, light intensity: about 10$^{-9}$ einstein●s$^{-1}$) from a xenon lamp, it was found that the photohydrogen●deuterium (H/D) exchange reaction rapidly proceeded, in the same manner as in the case shown in FIG. 7(a).

Accordingly, it is confirmed from the above that the iridium hydride complex serves as a very high-sensitive photoacid generator.

Example 9

When the iridium hydride complex was dissolved in water at 25° C., the solubility was equal to or greater than 90 mg/3.5 mL of water (2.6% by weight). It is confirmed from the above that the iridium hydride complex exhibits high solubility in water. Also, solubility in methanol and acetonitrile was similarly examined, and high solubility is confirmed in either of the solvents, similarly to water.

The photoacid generator of the present invention exhibits an effect of showing excellent solubility in an organic solvent or water, as well as being highly sensitive to visible light.

INDUSTRIAL APPLICABILITY

Because the iridium hydride complex of the present invention serves as a highly sensitive photoacid generator, and shows excellent solubility in water, an organic solvent or the like, it can be used as an acid generator for chemically-amplified photoresists or color filters for liquid crystal, and in addition, can be widely applied in photographic-related or printing-related fields, or the like.

The invention claimed is:

1. A method for generating an acid, said method comprising:
   (a) providing a metal hydride complex of the following formula (I) dissolved in a solution consisting essentially of a solvent

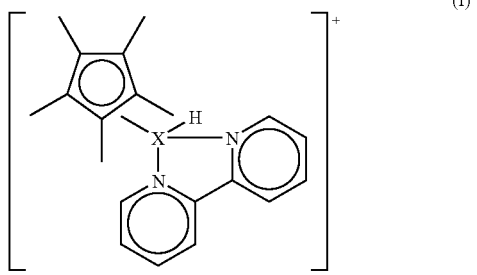

wherein X represents a metal atom; and
   (b) exciting the metal hydride complex by irradiating the complex with a laser beam until deprotonation of the metal hydride complex takes place; thereby
   (c) producing an acidic solution.

2. The method for generating acid of claim 1 wherein the metal hydride complex is dissolved in an organic solvent.

3. The method for generating an acid of claim 1, wherein the metal hydride complex is dissolved in water.

4. The method for generating an acid of claim 1, wherein the metal atom is iridium.

5. The method for generating an acid of claim 1, wherein the metal atom is ruthenium.

6. The method for generating an acid of claim 1, wherein the metal atom is rhodium.

7. The method for generating an acid of claim 1, wherein the metal atom is cobalt.

8. The method for generating an acid of claim 2, wherein the organic solvent is one or more of acetonitrile, a primary, secondary or tertiary alcohol, a polyhydric alcohol, dimethyl formamide, dimethyl sulfoxide and ethyl acetate.

9. A method for generating an acid for a chemically-amplified photoresist or a color filter for liquid crystals, said method comprising:
   (a) providing a metal hydride complex of formula (I) dissolved in a solution consisting essentially of a solvent

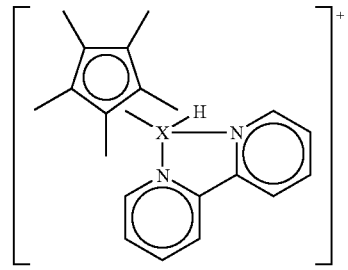

wherein X represents a metal atom; and
   (b) exciting the metal hydride complex by irradiating the complex with a laser beam until deprotonation of the metal hydride complex takes place; thereby
   (c) producing an acidic solution.

10. The method for generating an acid for a chemically-amplified photoresist or a color filter for liquid crystals of claim 9, wherein the metal atom is iridium.

11. The method for generating an acid for a chemically-amplified photoresist or a color filter for liquid crystals of claim 9, wherein the metal atom is ruthenium.

12. The method for generating an acid for a chemically-amplified photoresist or a color filter for liquid crystals of claim 9, wherein the metal atom is rhodium.

13. The method for generating an acid for a chemically-amplified photoresist or a color filter for liquid crystals of claim 9, wherein the metal atom is cobalt.

14. The method for generating acid of claim 9, wherein the metal hydride complex is dissolved in an organic solvent.

15. The method for generating acid of claim 9, wherein the metal hydride complex is dissolved in water.

16. The method for generating acid of claim 14, wherein the organic solvent is one or more of acetonitrile, a primary, secondary or tertiary alcohol, a polyhydric alcohol, dimethyl formamide, dimethyl sulfoxide and ethyl acetate.

17. The method for generating acid of claim 2, wherein the organic solvent is methanol.

18. The method for generating an acid of claim 14, wherein the organic solvent is methanol.

19. A method for generating an acid, said method comprising:
   (a) providing a metal hydride complex of the following formula (I) in solution

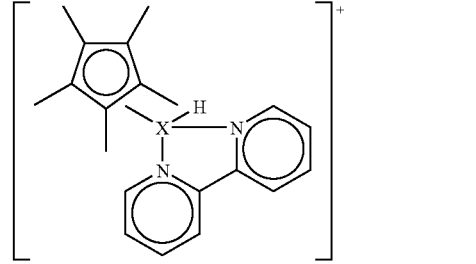

wherein X represents a metal atom; and
   (b) exciting the metal hydride complex by irradiating the complex with a laser beam until deprotonation of the metal hydride complex takes place wherein deprotonation is caused only by excitation by said laser beam; thereby
   (c) producing an acidic solution.

20. A method for generating an acid, said method consisting essentially of:
   (a) providing a metal hydride complex of the following formula (I) in solution

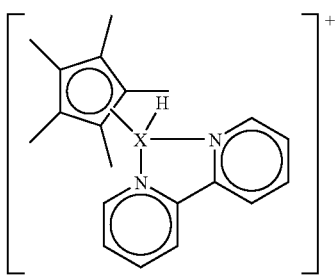

wherein X represents a metal atom; and (b) exciting the metal hydride complex by irradiating the complex with a laser beam until deprotonation of the metal hydride complex takes place; thereby (c) producing an acidic solution.

21. A method for generating an acid for a chemically-amplified photoresist or a color filter for liquid crystals, said method comprising:

(a) providing a metal hydride complex of formula (I) in solution

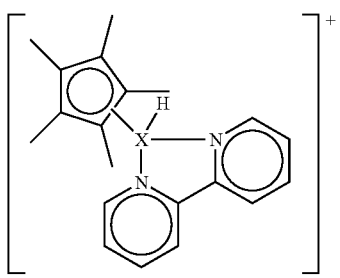

wherein X represents a metal atom; and (b) exciting the metal hydride complex by irradiating the complex with a laser beam until deprotonation of the metal hydride complex takes place wherein deprotonation is caused only by excitation by said laser beam; thereby (c) producing an acidic solution.

22. A method for generating an acid for a chemically-amplified photoresist or a color filter for liquid crystals, said method consisting essentially of:

(a) providing a metal hydride complex of formula (I) in solution

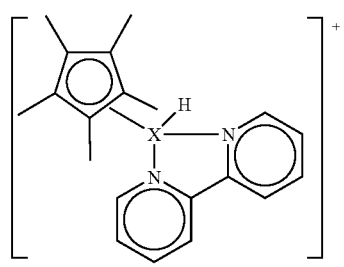

wherein X represents a metal atom; and (b) exciting the metal hydride complex by irradiating the complex with a laser beam until deprotonation of the metal hydride complex takes place; thereby (c) producing an acidic solution.

* * * * *